United States Patent
Wagner et al.

(10) Patent No.: US 11,883,224 B2
(45) Date of Patent: Jan. 30, 2024

(54) SYSTEM AND METHOD FOR FLOW-RESOLVED, THREE-DIMENSIONAL IMAGING

(71) Applicant: WISCONSIN ALUMNI RESEARCH FOUNDATION, Madison, WI (US)

(72) Inventors: Martin Wagner, Madison, WI (US); Paul Laeseke, Madison, WI (US); Michael Speidel, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 347 days.

(21) Appl. No.: 17/395,980

(22) Filed: Aug. 6, 2021

(65) Prior Publication Data
US 2023/0042953 A1    Feb. 9, 2023

(51) Int. Cl.
*A61B 6/00*  (2006.01)
*G06T 7/00*  (2017.01)

(52) U.S. Cl.
CPC ............ *A61B 6/5217* (2013.01); *A61B 6/504* (2013.01); *G06T 7/0016* (2013.01); *G06T 2207/10081* (2013.01); *G06T 2207/30104* (2013.01)

(58) Field of Classification Search
CPC ......... G06T 11/003–008; G06T 7/0012; G06T 7/0016
See application file for complete search history.

(56) References Cited

U.S. PATENT DOCUMENTS

2021/0307712 A1*  10/2021  Speidel ................. A61B 6/481

OTHER PUBLICATIONS

Li, Yinsheng, et al. "Mask free intravenous 3D digital subtraction angiography (IV 3D-DSA) from a single C-arm acquisition." Medical Imaging 2016: Physics of Medical Imaging. vol. 9783. SPIE, 2016.*
Garrett, John W., et al. "Quantitative blood flow imaging with time-resolved C-arm cone-beam CT imaging." Medical Imaging 2020: Physics of Medical Imaging. vol. 11312. SPIE, 2020.*
Çiçek et al., 3D U-Net: Learning Dense Volumetric Segmentation from Sparse Annotation, In Medical Image Computing and Computer-Assisted Intervention—MICCAI 2016: 19th International Conference, Athens, Greece, Oct. 17-21, 2016, Proceedings, Part II 19, pp. 424-432.
Hoffman et al., A Technique for Intra-Procedural Blood Velocity Quantitation Using Time-Resolved 2D Digital Subtraction Angiography, CVIR Endovascular, 2021, 4:11, 10 pages.

(Continued)

*Primary Examiner* — Carolyn A Pehlke
(74) *Attorney, Agent, or Firm* — Quarles & Brady, LLP

(57) ABSTRACT

A system and method are provided for creating an image including quantified flow within vessels of a subject. The method includes providing a single-sweep, three-dimensional (3D) image volume acquired from a subject during a single pass of a computed tomography (CT) imaging system as the subject receives a dose of a contrast agent and determining a phase shift corresponding to pulsatile contrast in vessels within the single-sweep, 3D image volume. The method further includes quantifying a flow through the vessels within the single-sweep, 3D image volume using the phase shift and generating a report including indicating flow through the vessels within the 3D image volume.

30 Claims, 7 Drawing Sheets

(56) References Cited

OTHER PUBLICATIONS

Jacobs et al., A Fast Algorithm to Calculate the Exact Radiological Path Through a Pixel or Voxel Space, Journal of Computing and Information Technology, 1998, 6(1):89-94.
Jin et al., Chemoembolization Endpoints: Effect on Survival Among Patients with Hepatocellular Carcinoma, American Journal of Roentgenology, 2011, 196(4):919-928.
Johnson et al., Microvascular Perfusion Changes Following Transarterial Hepatic Tumor Embolization, Journal of Vascular and Interventional Radiology, 2016, 27(1):133-141.
Li et al., An Enhanced SMART-RECON Algorithm for Time-Resolved C-Arm Cone-Beam CT Imaging, IEEE Transactions on Medical Imaging, 2020, 39(6):1894-1905.
Mistretta et al., 4D-DSA and 4D Fluoroscopy: Preliminary Implementation, Medical Imaging 2010: Physics of Medical Imaging, Proc. of SPIE, vol. 7622, pp. 1-8.
Periyasamy et al., A Quantitative Digital Subtraction Angiography Technique for Characterizing Reduction in Hepatic Arterial Blood Flow During Transarterial Embolization, Cardiovasc Intervent Radiol, 2021, 44(2):310-317.
Shaughnessy et al., Measuring Blood Velocity Using 4D-DSA: A Feasibility Study, Med. Phys., 2018, 45(10):4510-4518.
Wu et al., Quantification of Blood Velocity with 4D Digital Subtraction Angiography Using the Shifted Least-Squares Method, AJNR Am J Neuroradiol, 2018, 39:1871-1877.

\* cited by examiner

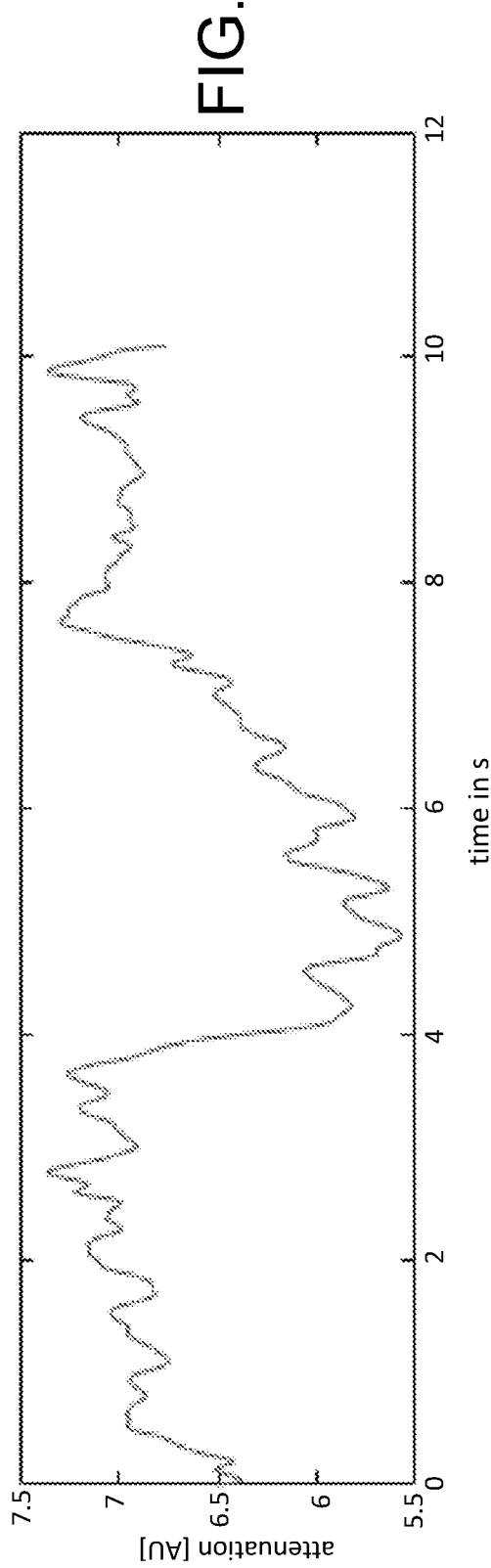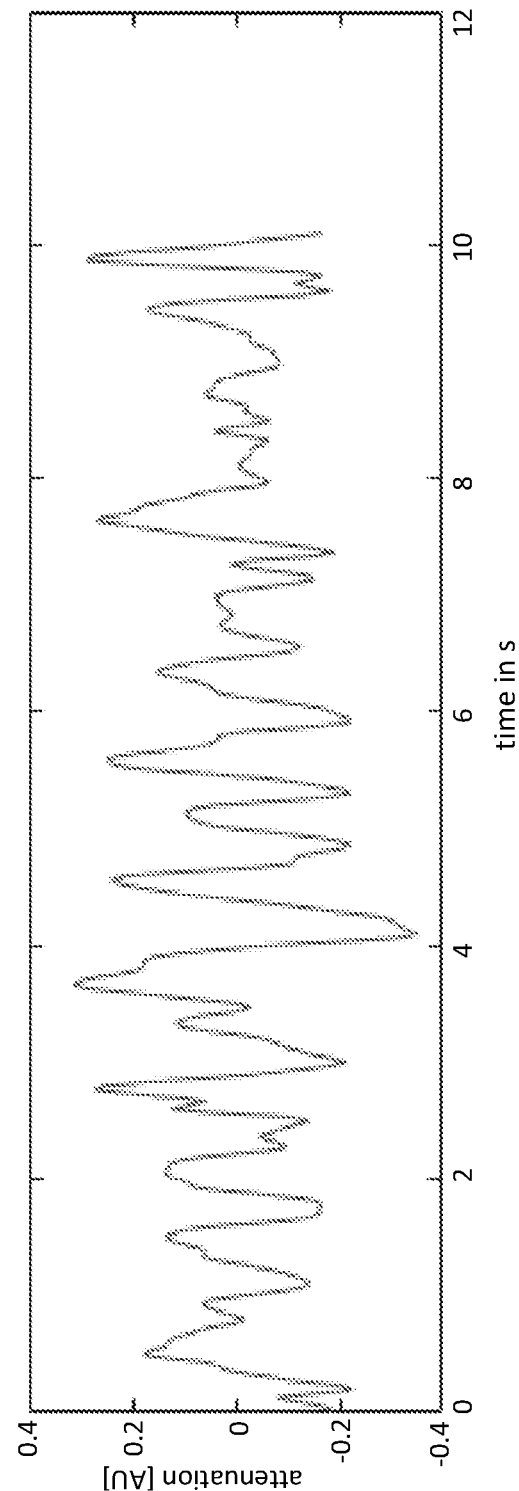

SYSTEM AND METHOD FOR FLOW-RESOLVED, THREE-DIMENSIONAL IMAGING

STATEMENT REGARDING FEDERALLY SPONSORED RESEARCH

This invention was made with government support under EB024677 awarded by the National Institutes of Health. The government has certain rights in the invention.

BACKGROUND

The present disclosure relates to systems and methods for medical image data acquisition and/or reconstruction. More particularly, systems and methods are provided for producing medical images that are flow-resolved and three-dimensional (3D), thereby, providing four-dimensional (4D) images.

Clinical outcomes for many conditions are directly correlated to the amount of accurate information that is available to a clinician and the speed with which the information or updated information can be provided. The ability to successfully diagnose and treat vascular conditions is highly dependent upon detailed and accurate information being available to clinicians. Furthermore, the dependence upon and availability of accurate information is important in both the diagnostic and treatment phases. Medical imaging is one of the key clinically-available sources of the information necessary to diagnose and treat patients.

Conventional 2D projection x-ray imaging, generally two-dimensional (2D) digital subtraction angiography (DSA) uses an injected contrast agent to visualize the flow of blood, and can be performed in the interventional suite. However, the 2D DSA image does not provide a complete picture of the complex three-dimensional (3D) flow patterns. At best, quantitative 2D DSA does not provide information on true 3D vessel path lengths and cross-sectional parameters which are required for accurate velocity and flow calculation.

More recently, time-resolved or "4D" DSA technology can be coupled with separate flow information to provide time-resolved imaging of contrast agent flow through a 3D vascular tree. However, 4D DSA can be limited in some clinical applications by the requirement for two separate rotational C-arm sweeps, which necessitates acquisition times sufficient to complete both sweeps and the radiation exposure associated with two sweeps. This challenge with using 4D DSA in some clinical application can be particularly acute if multiple 4D DSA acquisitions are required during a single treatment. For example, for treatments in the thorax, the multi-sweep acquisition times required by 4D DSA make its application limited in many clinical instances. This challenge with multi-sweep acquisitions in the thorax is further compounded by the fact that long acquisition times make it harder for the patient to perform a breath hold that extends through the whole acquisition. As a result, respiratory motion can cause artifacts in the images, Therefore, it would be desirable to have systems and methods for producing 3D images showing flow that are compatible with an interventional setting to provide clinicians with new and valuable information that can guide the intervention.

SUMMARY

The present disclosure overcomes the aforementioned drawbacks by providing systems and methods for generating flow-resolved, three-dimensional (3D) image volumes from computed tomographic (CT) or cone-beam CT (CBCT) data without needing multiple acquisitions, such as to acquire both a non-contrast data set and a contrast-enhanced dataset. That is, present disclosure overcomes the aforementioned drawbacks by providing systems and methods for generating flow-resolved, 3D image volumes from single-sweep, 3D CT or CBCT datasets. Using the systems and methods provided herein, flow dynamics can be identified and even quantified from a single-sweep, 3D CT dataset without subtraction of a "mask" or "non-contrast" dataset.

In accordance with one aspect of the present disclosure, a system is provided for acquiring images of three-dimensional flow within an interior volume of a subject. The system includes an x-ray imaging system configured to acquire images from the subject and a computer system. The computer system is configured to control the x-ray imaging system to perform a single sweep of the subject to acquire a single-sweep, three-dimensional (3D) image dataset and reconstruct the single-sweep, 3D image dataset into a 3D image volume. The computer system is further configured to determine a phase shift corresponding to pulsatile contrast in vessels within the 3D image volume, quantify a flow through the vessels within the 3D image volume using the phase shift, and generate a report including quantified flow through the vessels within the 3D image volume.

In accordance with another aspect of the present disclosure, a method is provided for creating an image including quantified flow within vessels of a subject. The method includes providing a single-sweep, three-dimensional (3D) image volume acquired from a subject during a single pass of a computed tomography (CT) imaging system as the subject receives a dose of a contrast agent and determining a phase shift corresponding to pulsatile contrast in vessels within the single-sweep, 3D image volume. The method further includes quantifying a flow through the vessels within the single-sweep, 3D image volume using the phase shift and generating a report including indicating flow through the vessels within the 3D image volume.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 5A is a graph showing an example of a time-attenuation curve that is "contaminated" with background signal from organs and other anatomical structures.

FIG. 5B is a graph showing the same time-attenuation curve after being subject to a high-pass filter, clearly showing pulsatile signal of contrast in vessels.

DETAILED DESCRIPTION

Figure 1A:
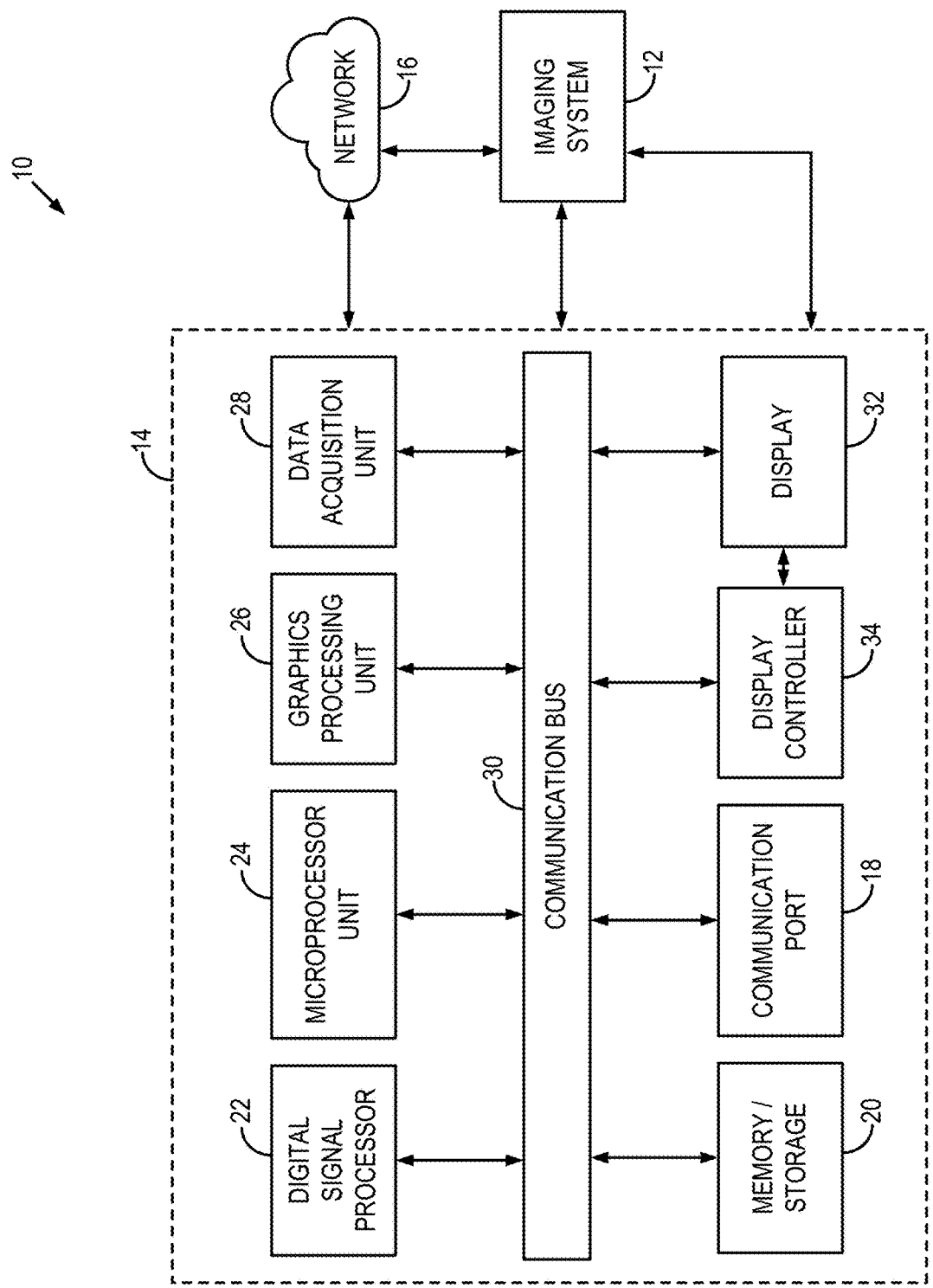
FIG. 1A is a schematic diagram of an example system in accordance with the present disclosure and that can be configured to implement the methods described herein.

Referring now to FIG. 1A, a block diagram of an example system 10 is provided that can be configured to carry out techniques, methods, and processes accordance with the present disclosure. The system may include an imaging system 12 that is coupled to a computer system 14. The coupling of the imaging system 12 to the computer system 14 may be a direct or dedicated network connection, or may be through a broad network 16, such as an intranet or the Internet.

The computer system 14 may be a workstation integrated with or separate from the medical imaging systems 12 or a variety of other medical imaging systems, including, as non-limiting examples, either gantry-based or C-arm computed tomography (CT) systems and the like. The CT system can be configured to utilize a fan or cone beam or other beam geometry. Relatedly, "CT data" or "CT dataset" may refer to 2D data or 3D data, or the like. As used herein "CT" or "CT data" or "CT dataset" can be used in reference to any of these system, acquisition implementations, or data unless specifying otherwise.

The computer system 14 may be a workstation integrated within the medical imaging system 12 or may be a separate workstation or mobile device or computing system. To this end, the following description of particular hardware and configurations of the hardware of the example computer system 14 is for illustrative purposes. Some computer systems may have varied, combined, or different hardware configurations, and may include commercially-available computer systems or specialized computer systems.

Medical imaging data acquired by the medical imaging system 12 or other imaging system and can be provided to the computer system 14, such as over the network 16 or from a storage device. To this end, the computer system 14 may include a communications port or other input port 18 for communication with the network 16 and system coupled thereto. Also, the computer system 14 may include memory and storage capacity 20 to store and access data or images.

In some configuration, computer system 14 may include one or more processing systems or subsystems. That is, the computer system 14 may include one or more physical or virtual processors. As an example, the computer system 14 may include one or more of a digital signal processor (DSP) 22, a microprocessor unit (MPU) 24, and a graphics processing unit (GPU) 26 (or other processors, such as field programmable gate arrays (FPGAs)). If the computer system 14 is integrated into the medical imaging system, a data acquisition unit 28 may be connected directly to the above-described processor(s) 22, 24, 26 over a communications bus 30, instead of communicating acquired data or images via the network 16. As an example, the communication bus 30 can be a group of wires, or hardwire used for switching data between the peripherals or between any components, such as the communication buses described above.

The computer system 14 may also include or be connected to a display 32. To this end, the computer system 14 may include a display controller 34. The display 32 may be a monitor connected to the computer system 14 or maybe integrated with the computer system 14, such as in portable computers or mobile devices.

Figure 1B:
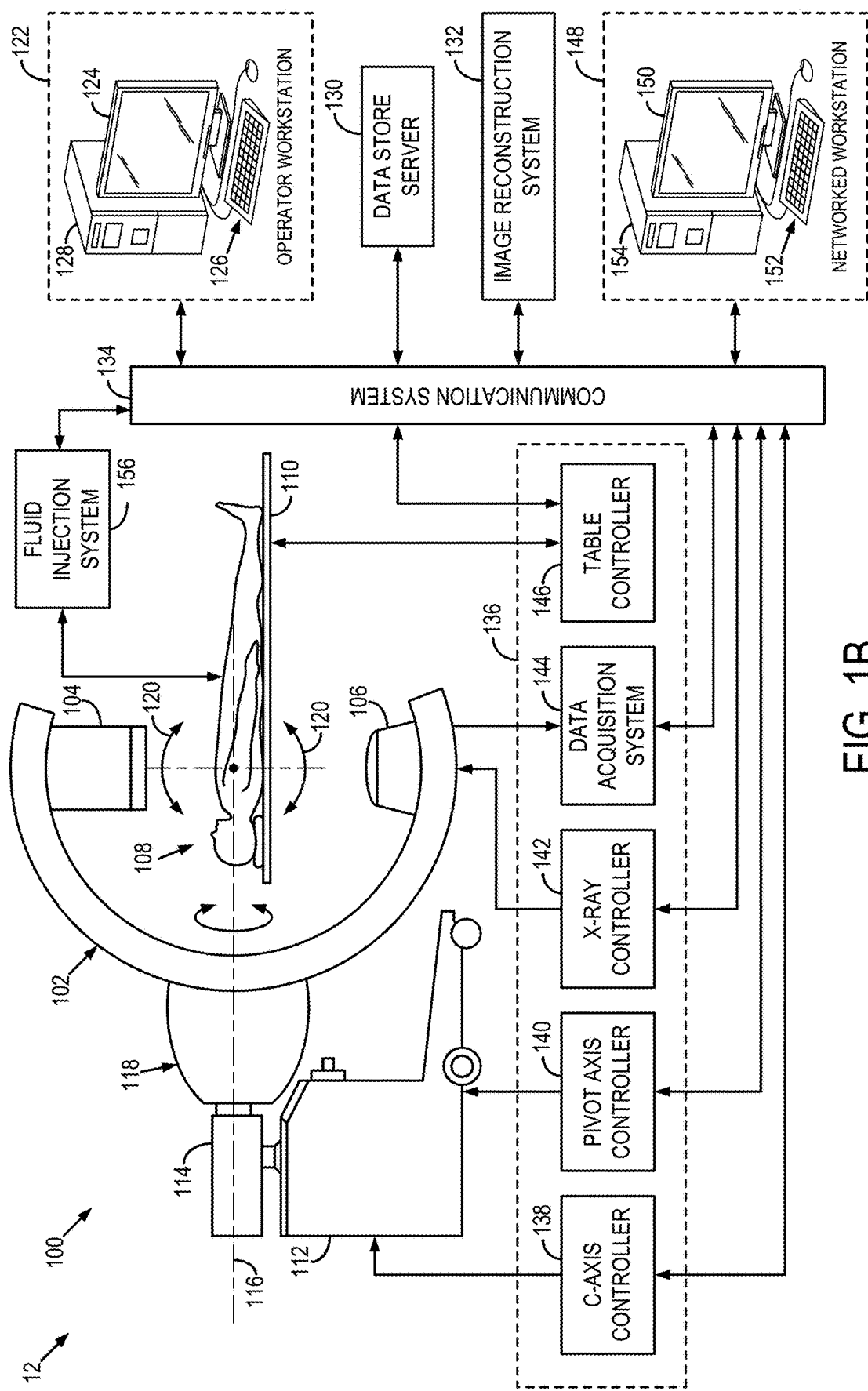
FIG. 1B is a schematic diagram of a x-ray computed tomography (CT) imaging system that can be configured in accordance with the present disclosure.

Referring to FIG. 1B, one, non-limiting example of the imaging system 12 is provided. Specifically, in this example, a so-called "C-arm" x-ray imaging system 100 is illustrated for use in accordance with some aspects of the present disclosure. However, the systems and methods provided herein are not limited to a particular structure or architecture of x-ray imaging system. That is, in the illustrated configuration, the imaging system 12 is generally designed for use in connection with interventional procedures. However, non-interventional systems, such as "closed" systems may also be used with the systems and methods described herein.

Thus, in the non-limiting example illustrated in FIG. 1B, the imaging system 12 forms a C-arm CT imaging system 100 that includes a gantry 102 to which an x-ray source assembly 104 is coupled on one end and an x-ray detector array assembly 106 is coupled at its other end. The gantry 102 enables the x-ray source assembly 104 and detector array assembly 106 to be oriented in different positions and angles around a subject 108, such as a medical patient or an object undergoing examination, which is positioned on a table 110. When the subject 108 is a medical patient, this configuration enables a physician access to the subject 108.

The x-ray source assembly 104 includes at least one x-ray source that projects an x-ray beam, which may be a beam, fan-beam, or cone-beam of x-rays, towards the x-ray detector array assembly 106 on the opposite side of the gantry 102. The x-ray detector array assembly 106 includes at least one x-ray detector, which may include a number of x-ray detector elements. Examples of x-ray detectors that may be included in the x-ray detector array assembly 106 include flat panel detectors, such as so-called "small flat panel" detectors.

Together, the x-ray detector elements in the one or more x-ray detectors housed in the x-ray detector array assembly 106 sense the projected x-rays that pass through a subject 108. Each x-ray detector element produces an electrical signal that may represent the intensity of an impinging x-ray beam and, thus, the attenuation of the x-ray beam as it passes through the subject 108. In some configurations, each x-ray detector element is capable of counting the number of x-ray photons that impinge upon the detector. During a scan to acquire x-ray projection data, the gantry 102 and the components mounted thereon rotate about an isocenter of the C-arm x-ray imaging system 100.

The gantry 102 includes a support base 112. A support arm 114 is rotatably fastened to the support base 112 for rotation about a horizontal pivot axis 116. The pivot axis 116 is aligned with the centerline of the table 110 and the support arm 114 extends radially outward from the pivot axis 116 to support a drive assembly 118 on its outer end. The gantry 102 is fastened to the drive assembly 118 and is coupled to a drive motor (not shown) that slides the gantry 102 to revolve it about a C-axis, as indicated by arrows 120. The pivot axis 116 and C-axis are orthogonal and intersect each other at the isocenter of the x-ray imaging system 100, which is indicated by the black circle and is located above the table 110.

The x-ray source assembly 104 and x-ray detector array assembly 106 extend radially inward to the pivot axis 116 such that the center ray of this x-ray beam passes through the system isocenter. The center ray of the x-ray beam can thus be rotated about the system isocenter around either the pivot axis 116, the C-axis, or both during the acquisition of x-ray attenuation data from a subject 108 placed on the table 110. During a scan, the x-ray source and detector array are rotated about the system isocenter to acquire x-ray attenuation projection data from different angles. The imaging system 12 may include or be used with a fluid injection system 156. The fluid injection system 156 may deliver a fluid, such as a contrast agent, to the subject during the imaging acquisition The x-ray imaging system 100 also includes an operator workstation 122, which typically includes a display 124, one or more input devices 126, such as a keyboard and mouse; and a computer processor 128. The computer processor 128 may include a commercially available programmable machine running a commercially available operating system. The operator workstation 122 provides the operator interface that enables scanning control parameters to be entered into the C-arm x-ray imaging system 100. In general, the operator workstation 122 is in communication with a data store server 130 and an image reconstruction system 132. By way of example, the operator workstation 122, data store server 130, and image reconstruction system 132 may be connected via a communication system 134, which may include any suitable network connection, whether wired, wireless, or a combination of both. As an example, the communication system 134 may include both proprietary or dedicated networks, as well as open networks, such as the internet.

The operator workstation 122 is also in communication with a control system 136 that controls operation of the x-ray imaging system 100. The control system 136 generally includes a C-axis controller 138, a pivot axis controller 140, an x-ray controller 142, a data acquisition system ("DAS") 144, and a table controller 146. The x-ray controller 142 provides power and timing signals to the x-ray source assembly 104, and the table controller 146 is operable to move the table 110 to different positions and orientations within the x-ray imaging system 100.

The rotation of the gantry 102 to which the x-ray source assembly 104 and the x-ray detector array assembly 106 are coupled is controlled by the C-axis controller 138 and the pivot axis controller 140, which respectively control the rotation of the gantry 102 about the C-axis and the pivot axis 116. In response to motion commands from the operator workstation 122, the C-axis controller 138 and the pivot axis controller 140 provide power to motors in the C-arm x-ray imaging system 100 that produce the rotations about the C-axis and the pivot axis 116, respectively. For example, a program executed by the operator workstation 122 generates motion commands to the C-axis controller 138 and pivot axis controller 140 to move the gantry 102, and thereby the x-ray source assembly 104 and x-ray detector array assembly 106, in a prescribed scan path.

The DAS 144 samples data from the one or more x-ray detectors in the x-ray detector array assembly 106 and converts the data to digital signals for subsequent processing. For instance, digitized x-ray data is communicated from the DAS 144 to the data store server 130. The image reconstruction system 132 then retrieves the x-ray data from the data store server 130 and reconstructs an image therefrom. The image reconstruction system 130 may include a commercially available computer processor, or may be a highly parallel computer architecture, such as a system that includes multiple-core processors and massively parallel, high-density computing devices. Optionally, image reconstruction can also be performed on the processor 128 in the operator workstation 122. Reconstructed images can then be communicated back to the data store server 130 for storage or to the operator workstation 122 to be displayed to the operator or clinician.

The x-ray imaging system 100 may also include one or more networked workstations 148. By way of example, a networked workstation 148 may include a display 150; one or more input devices 152, such as a keyboard and mouse; and a processor 154. The networked workstation 148 may be located within the same facility as the operator workstation 122, or in a different facility, such as a different healthcare institution or clinic.

The networked workstation 148, whether within the same facility or in a different facility as the operator workstation 122, may gain remote access to the data store server 130, the image reconstruction system 132, or both via the communication system 134. Accordingly, multiple networked workstations 148 may have access to the data store server 130, the image reconstruction system 132, or both. In this manner, x-ray data, reconstructed images, or other data may be exchanged between the data store server 130, the image reconstruction system 132, and the networked workstations 148, such that the data or images may be remotely processed by the networked workstation 148. This data may be exchanged in any suitable format, such as in accordance with the transmission control protocol ("TCP"), the Internet protocol ("IP"), or other known or suitable protocols.

As will be described, the systems and methods of the present disclosure are particularly useful in a variety of different clinical settings. For example, liver embolization (e.g., transarterial chemoembolization (TACE)) is an effective, minimally invasive treatment option for patients with intermediate or advanced cancer (e.g., hepatocellular carcinoma (HCC)) and select patients with liver metastases. Angiographic monitoring of residual blood flow to treated tumors is important to the success of the procedure and impacts outcomes. However, outcomes are tied to good visualization of eliminating blood flow to the tumor using angiography. While efforts have been made to standardize the angiographic endpoint for liver embolization, it remains largely subjective and is not reproducible. In particular, perfusion and patency of the tumor microvasculature depend on the degree of stasis achieved on angiography.

To address this need for understanding the tumor microvaculature, some have attempted to use digital subtraction angiography (DSA), both 2D and 4D. For example, quantitative 2D DSA has been proposed as means to produce quantitative endpoints for liver embolization. Quantitative 2D DSA does not provide information on true 3D vessel path lengths and cross-sectional parameters, which are required for accurate velocity and flow calculation. While 4D DSA could provide 3D blood flow information, its usability is limited by the requirement for two separate C-arm sweeps (non-contrast (mask) and contrast enhanced (fill)), which increase radiation exposure to the patient (especially if multiple 4D DSA acquisitions are required during a single treatment). It also increases acquisition time, which is crucial for procedures in the thorax and abdomen where respiratory motion can cause severe reconstruction artifacts.

As will be described, the present disclosure provides systems and methods that can utilize a single imaging sweep (for example, a single C-arm sweep) and produce a 4D (3D+time-resolved flow) image. Thus, the systems and methods provided herein overcome the shortcomings of 2D DSA by providing the needed 4D images. Furthermore, the systems and methods provided herein overcome the shortcomings of prior 4D imaging attempts, such as 4D DSA, by generating the 4D images from the data acquired with only one imaging sweep, thereby doing so with lower radiation dose and more efficiently than prior attempts, such as using 4D DSA. The systems and methods provided herein provide accurate blood flow and velocity measurement where prior systems and methods have not.

Figure 2:
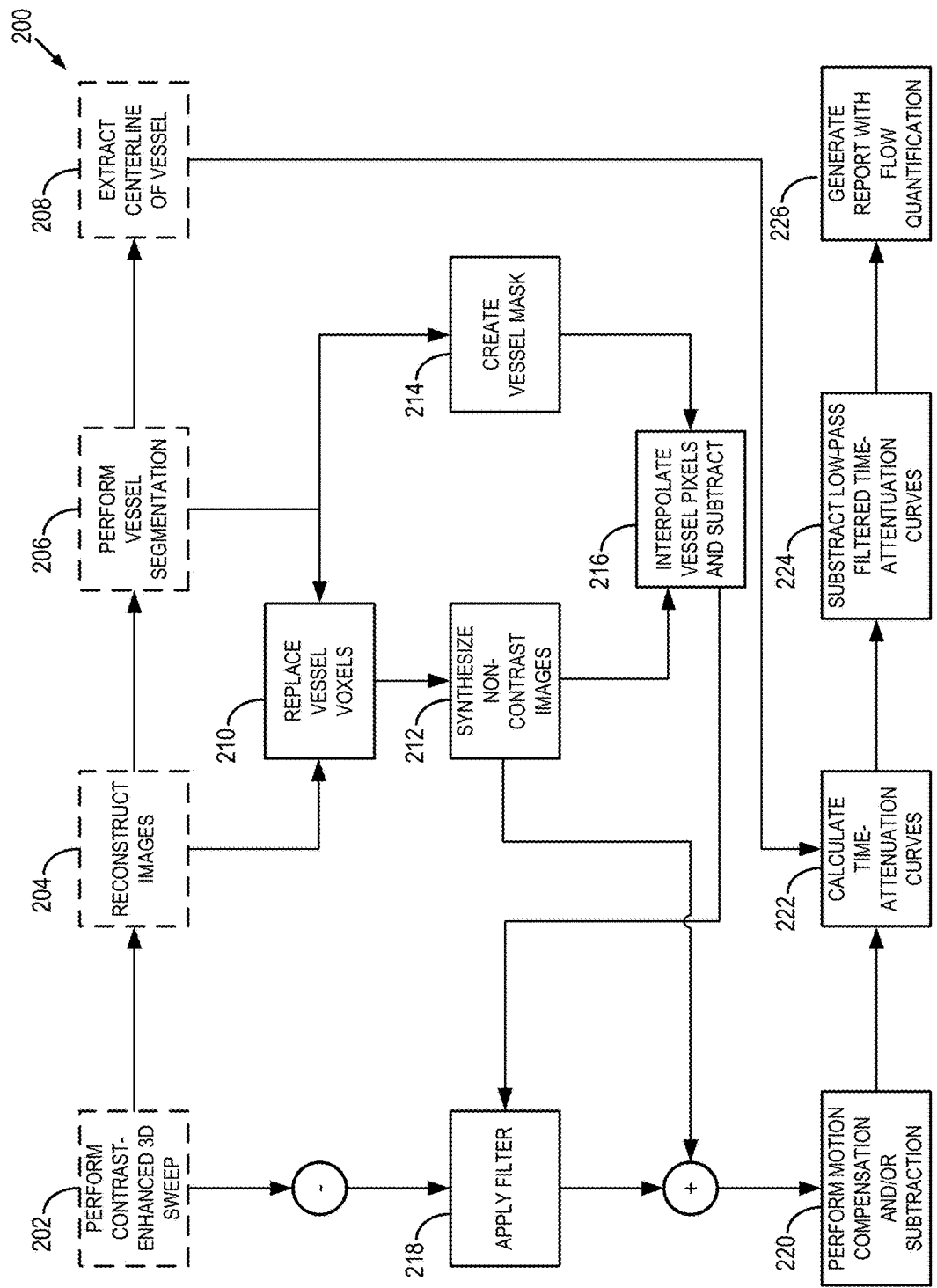
FIG. 2 is a process diagram for a non-limiting example of a process in accordance with the present disclosure for single-sweep 4D angiography.

Referring now to FIG. 2, a process diagram is provided for a process 200 in accordance with the present disclosure for single-sweep 4D angiography. The process includes acquiring imaging data. In one non limiting example, the imaging data may be acquired using a rotational C-arm CT system, with contrast injection performed. In accordance with the present disclosure, a single-sweep acquisition may be performed with contrast present. Unlike the systems and methods described above, a pre-contrast acquisition or separate mask acquisition is not required.

In one non-limiting example, the CT acquisition may be a cone beam CT (CBCT) acquisition. Also, in a non-limiting example, the acquisition may be performed over a 260-degree gantry rotation providing projection images from, for example, 304 angles.

Once the imaging data is acquired at process step 202, images may be reconstructed at process block 204. In one non-limiting example, reconstruction may include a conventional filtered back projection (FBP) reconstruction. The resulting images form 3D volume that can then be used at process block 206 to perform vessel segmentation. In accordance with one non-limiting example, the vessel segmentation may be performed using a deep learning-based vessel segmentation network. In one non-limiting example, the network may use a U-net architecture and be trained using previous 3D acquisitions, whether using the present systems and methods or even DSA or other techniques. The result of the vessel segmentation at process block 206 is a binary representation of the vasculature, which can then be used at process block 208 to extract vessel centerlines. Notably, process blocks 202-208 may be performed as described or may be performed via other steps that likewise deliver the reconstructed image, vessel segmentation, and centerline extractions. As just one example, it is possible that process blocks 202-208 may be omitted or considered optional, as some other systems or methods may be used to yield the desired results.

Thus, irrespective of the particular processes used to generate the 3D data, reconstructed images from the 3D data, segmented vessels, and centerline extractions, the following steps are performed to synthesize non-contrast projection images from the 3D reconstruction and the vessel anatomy. At process block 210, this process is performed by replacing vessel voxels from the vessel segmentation with an attenuation value representing non-contrast enhanced blood. The attention value may be a constant. Then, at process block 212, non-contrast images are synthesized. For example, a digital forward projection can be performed using a Siddon ray tracing approach. As one non-limiting example, such as Siddon ray tracing approach is described, for example, in F. Jacobs, E. Sundermann, B. De Sutter, M. Christiaens, and I. Lemahieu, "A fast algorithm to calculate the exact radiological path through a pixel or voxel space," CIT. Journal of computing and information technology, vol. 6, no. 1, Art. no. 1, 1998, which is incorporated herein by reference in its entirety.

To the extent that there is truncation in the images, such as caused by the limited field of view of the 3D reconstruction, or patient motion (e.g., respiratory motion, other physiological motion, or bulk motion), artifacts may be seen in the digital projections. As such, truncation and motion correction can be performed. At process block 214, a forward projection of the 3D binary vessel mask into the 2D image space may be performed. Then, at process block 216, pixels in the original projection images may be replaced using interpolation and subtracting the result from the synthesized projection images. At process block 218, a median filter can be applied using the raw imaging data to extract the low frequency components expected due to truncation.

Then, at process block 220, the estimated offset can be added to the synthesized images from process block 212 to create truncation corrected non-contrast projection images. A block-matching based motion-compensation approach can be performed between the original projection images and the synthesized masks to account for small involuntary patient motion and the registered images are subsequently subtracted to extract the contrast (e.g., iodine) signal only.

At process block 222, time-attenuation curves (TACs) can then be calculated for each point along the vessel centerlines from process block 208, for example, by forward projecting the points into the 2D image space, interpolating the corresponding gray values, and normalizing by the number of voxels that contribute to each pixel. Since each projection is acquired at a different point in time, this generates a time-dependent curve of the iodine enhancement at each point along the centerline. To isolate the pulsatile signal used for flow quantification in each TAC, the TACs can be low-pass filtered at process block 224, for example, using a moving average filter. The result is subtracted from the original TAC to yield the desired TACs. Finally, at process block 226, a report can be generated that includes flow quantification. For example, flow quantification can be estimating using the phase shift of the pulsatile signal in frequency space compared to the distance along the vessel centerlines.

Figures 3A, 3B, 3C:
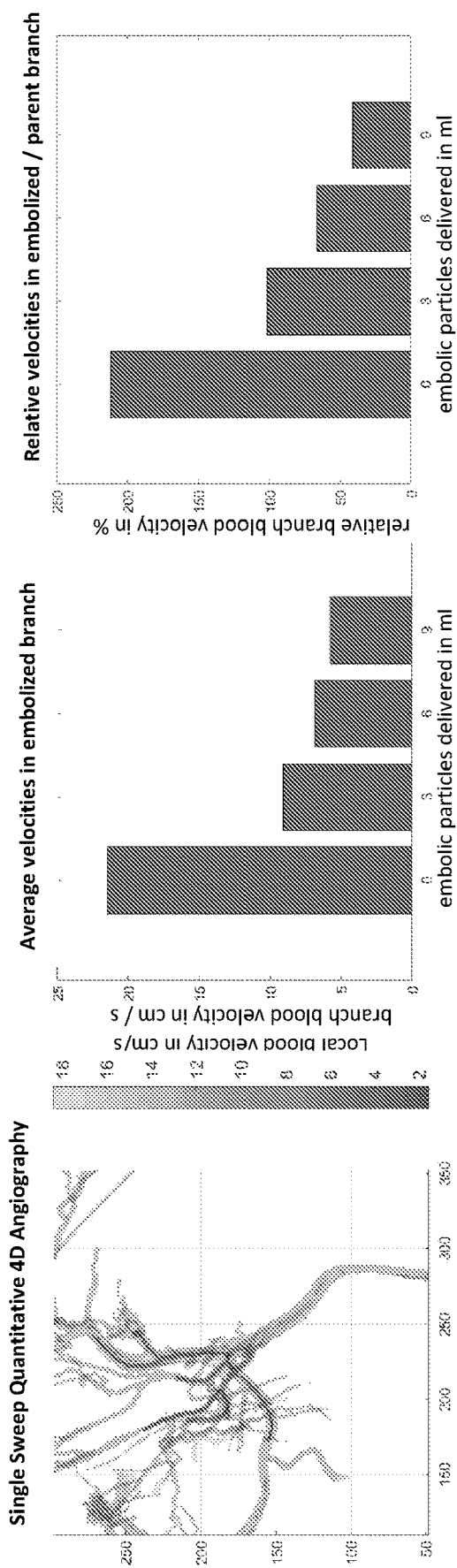
FIG. 3A is a non-limiting example of an image including color overlays of quantified blood-flow velocity that may form part of a report in accordance with the present disclosure.
FIG. 3B is a graph showing a comparison of the average blood velocity in an embolized branch after different levels of embolization.
FIG. 3C is a graph showing a comparison of the relative velocities calculated by dividing the average velocity of the embolized branch by the average velocity of the parent branch resulting in a more linear relationship between embolic particles delivered and blood velocity.

In one non-limiting example, the above-described process was applied to data where contrast enhanced CBCT acquisitions were acquired in regular intervals before, during, and after embolization. Specifically, acquisitions were performed after 0, 3, 6, and 9 ml of embolic particles were delivered. FIG. 3A shows one example of a quantified flow included in a 3D image of the vasculature with color-coded velocities positioned along vessel centerlines for all major vessel branches. Also, FIG. 3B is a graph showing a comparison of the average blood velocity in the embolized branch after different levels of embolization, showing a consistent decrease of velocity with increased embolization. Since, overall blood flow might not be constant over time, FIG. 3C is a graph showing a comparison of the relative velocities calculated by dividing the average velocity of the embolized branch by the average velocity of the parent branch resulting in a more linear relationship between embolic particles delivered and blood velocity.

Figure 4:
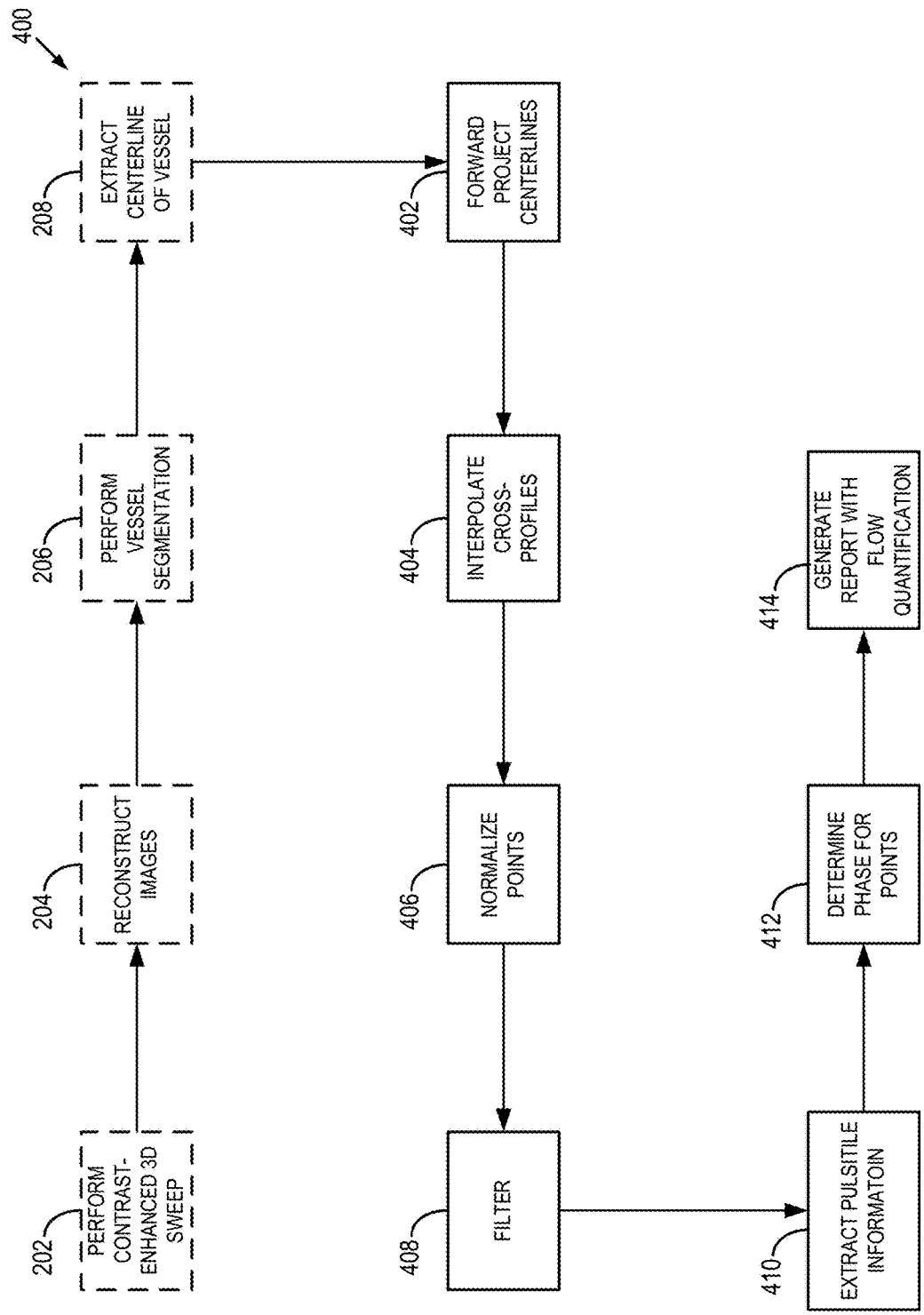
FIG. 4 is another process diagram for a non-limiting example of a process in accordance with the present disclosure for single-sweep 4D angiography.

The above-described systems and methods may be implemented in a variety of ways. Referring to FIG. 4, another process 400, alternative to the approach described with respect to FIG. 2, will be described. As described above with respect to FIG. 2, process block 202-208 may be performed. That is, the purpose of process blocks 202-208 is to extract the 3D geometry of the vasculature from a contrast enhanced cone beam CT (CBCT) reconstruction. Though the process 400 may use the same data and initial steps, the process 400 uses the single-sweep data to perform a signal extraction in temporal/frequency space, instead of a subtraction of a synthesized mask image. As will be described, time-attenuation curves (TACs) in this process 400 can be calculated directly from unsubtracted contrast-enhanced projection images and contaminating signal (for example, signal from other anatomic structures not related to the contrast in the vasculature) is filtered out in time and frequency space.

At process block 402, 3D vessel centerlines are forward projected into the projection image. By doing so, a cross-profile can be calculated for points along the centerlines. In particular, at process block 404, a vector perpendicular to the centerline at a given point is identified and contrast values (e.g., gray values) at spaced sampling points, for example, equally spaced points, are interpolated along this line. Values from sample points inside of the vessel can be normalized at process block 406. For example, values from sample points inside the vessel can be averaged to reduce noise. Optionally, the average value of points just outside the vessel can be subtracted to remove background signal. This can be readily achieved, for example, using vessel thickness, which can be determined from the 3D segmentations. The result is a time-attenuation curve (one time point for each projection image) for each point along the centerlines, which are still "contaminated" by signal from organs or other anatomical structures.

To further reduce the influence of other anatomical structures and extract the pulsatile signal from the contrast injection in the vessels, a filter is applied at process block 408, which removes low frequency changes in the contrast. For example, the filter may be a high-pass filter. In one non-limiting example, this can be achieved by subtracting a low pass filtered version of each TAC from the original TAC (e.g. moving average filter: approximately 1 s width). However, many other low-pass filters can also be used instead. The resulting curve is a "cleaned" time-attenuation curve showing the pulsatile contrast changes in the vessels. For example, FIG. 5A is a graph showing an example of a time-attenuation curve that is "contaminated" with background signal from organs and other anatomical structures. On the other hand, FIG. 5B is a graph showing the same time-attenuation curve after being subject to a high-pass filter, clearly showing pulsatile signal of contrast in vessels.

Figure 5C:
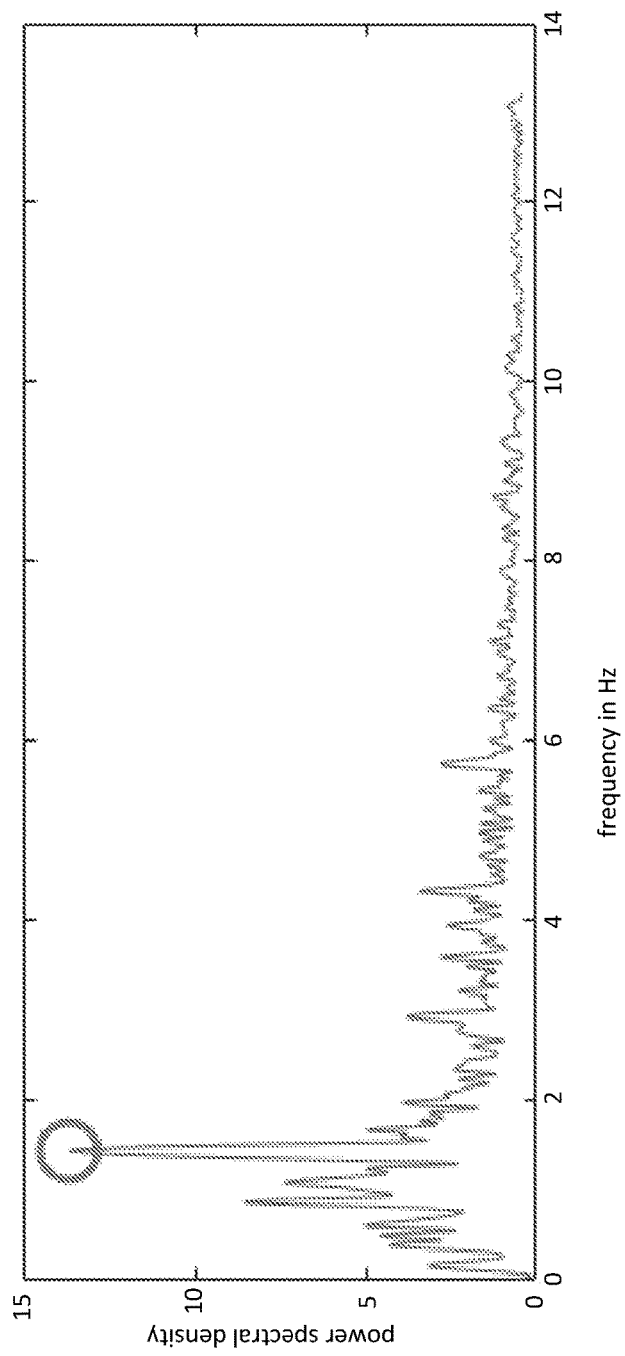
FIG. 5C is a graph showing that a 1D Fourier transform can be applied to each TAC and the average power spectrum over all centerline points (of a single centerline) can be calculated.

Referring again to FIG. 4, at process block 410, pulsatile information can be extracted. As one non-limiting example, a frequency-based analysis can be used to extract only the frequency corresponding to the pulsatile contrast changes in the vessels. For example, a 1D Fourier transform can be applied to each TAC and the average power spectrum over all centerline points (of a single centerline) can be calculated, as shown in FIG. 5C. In one non-limiting example, the frequency corresponding to the highest power spectral density can be used for further velocity and flow analysis.

Figure 5D:
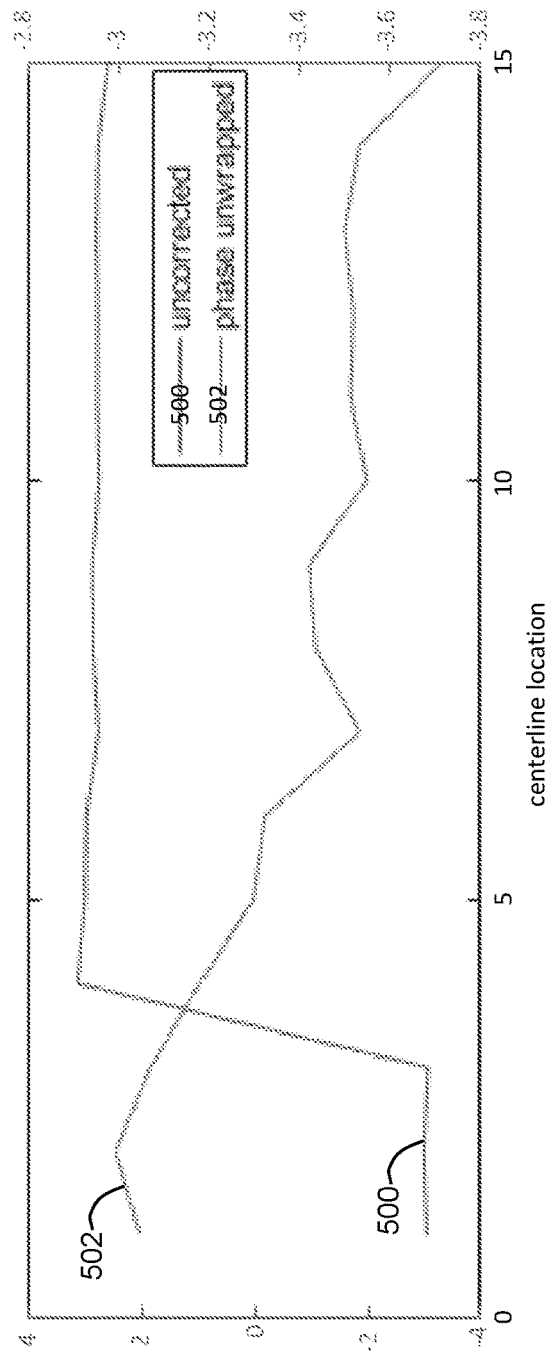
FIG. 5D is a graph showing a phase for a selected peak frequency at each centerline point with and without correction.

Flow velocities, for example, local flow velocities can then be calculated by determining the phase shift of the selected frequency along the centerline, at process block 412. In one non-limiting example, the phase corresponding to each point along the centerline can be extracted directly from the Fourier transform using the angular component of the selected frequency. Phase unwrapping can then be applied to remove any jumps in the phases along the centerline. For example, referring to FIG. 5D, the phase for the selected peak frequency at each centerline point without correction 500 is illustrated. Then, the phase for the selected peak frequency at each centerline point after phase unwrapping 502 is shown. In one non-limiting example, velocities can be calculated by fitting linear functions to sliding windows of the phase unwrapped curve 502. Finally, a function (linear function) can be fit to each sliding window along the centerline (e.g. 20 sample points window) to estimate local velocities (slope of the linear function). A smoothing spline can be fit to the estimated local velocities of a centerline to remove outliers and noise.

As a result, at process block 414, a report can be generated with flow quantification, including local flow quantification. The report may be an image with color, graphical, and/or numerical overlays, or a written report or table.

Therefore, the present disclosure provides systems and methods for 3D quantitative flow information for intraprocedural assessment of treatment progress and determination of endpoints. In doing so, the systems and methods provided herein provide consistent, quantitative information needed for procedures like embolization, where the degree of embolization is critical for the success of the procedure (under embolization may lead to tumor survival, while over embolization may cause necrosis of healthy tissue and increase the risk to the patient).

The systems and methods provided herein may be used as an external software package or integrated add-on to scanner or other systems associated with commercial CT systems, such as existing C-arm systems. During embolization procedures, acquisitions may be performed before, during, or after embolization. Data may be transferred to an external workstation where reconstruction is performed, and blood velocities can be displayed within minutes without interrupting the clinical workflow. Based on the resulting flow measurements additional embolization material may be injected until the desired endpoint is reached.

The present disclosure provides systems and methods not contemplated by the prior art. The systems and methods provided herein yield 4D (3D+time) reconstruction of arterial blood flow, and can include quantitative information regarding local blood flow and velocities, from a single contrast-enhanced cone beam CT sweep or scan. The systems and method provided herein do not require non-contrast, mask images to be acquired. Thus, proper visualization of blood flow is provided using a standardizable/repeatable angiographic process that does not subject the patient to the radiation dose of multiple sweeps/acquisitions and does not require the time to perform extended acquisitions. In the case of embolization, endpoints can be readily identified and tracked in an objective and reproducible way.

The systems and methods provided herein provide 3D time resolved contrast information that can be used for accurate blood flow and velocity measurement. Alternative subtraction-based techniques require separate mask runs to (1) reconstruct a subtracted 3D constraining volume showing only vessels and (2) isolate signal from blood (contrast) in the 2D projection images to generate time-concentration curves. In contrast to subtraction-based methods, such as 4D DSA, only a single C-arm sweep is used in the systems and methods provided herein, thus reducing radiation exposure, acquisition time, and risk of motion artifacts.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for acquiring images of three-dimensional flow within an interior volume of a subject, the system comprising:
an x-ray imaging system configured to acquire images from the subject; and
a computer system configured to:
control the x-ray imaging system to perform a single sweep of the subject to acquire a single-sweep, three-dimensional (3D) image dataset;
reconstruct the single-sweep, 3D image dataset into a 3D image volume;
determine a phase shift corresponding to pulsatile contrast in the vessels within the 3D image volume;
quantify a flow through the vessels within the 3D image volume using the phase shift; and
generate a report including quantified flow through the vessels within the 3D image volume.

2. The system of claim 1 wherein the computer is further programmed to generate synthesized non-contrast images from the single-sweep, 3D image dataset.

3. The system of claim 2 wherein the computer is further programmed to generate an attenuation value representing non-contrast enhanced blood from the single-sweep, 3D image dataset to generate the synthesized non-contrast images from the single-sweep, 3D image dataset.

4. The system of claim 2 wherein the computer is further programmed to subtract the 3D image volume and the synthesized non-contrast images from the single-sweep, 3D image dataset.

5. The system of claim 1 wherein the computer system is further programmed to generate time-attenuation curves (TACs) to determine the phase shift corresponding to pulsatile contrast in the vessels.

6. The system of claim 1 wherein the computer system is further programmed to determine a centerline for the vessels within the 3D image volume.

7. The system of claim 6 wherein the computer system is further programmed to determine a cross-profile for points along the centerline.

8. The system of claim 1 wherein the computer system is further programmed to perform a frequency-based analysis to extract only a frequency corresponding to the pulsatile contrast in the vessels.

9. The system of claim 8 wherein the computer system is further programmed to generate time-attenuation curves (TACs) for the vessels in the 3D image volume.

10. The system of claim 9 wherein the computer system is further programmed to apply a one-dimensional Fourier transform to each TAC and calculate an average power spectrum for the vessels in the 3D image volume to determine the phase shift corresponding to pulsatile contrast in vessels within the 3D image volume based on spectral power density.

11. The system of claim 1 wherein the computer system is further programmed to determine the phase shift corresponding to pulsatile contrast in vessels within the 3D image volume based on spectral power density by identifying a peak spectral power density.

12. The system of claim 11 wherein the computer system is further programmed to extract an angular component at a selected frequency using the peak spectral power density to determine the phase shift corresponding to pulsatile contrast in vessels within the 3D image volume.

13. The system of claim 1 wherein the computer system is further programmed to calculate a velocity of blood flow through vessels within the 3D image volume using a linear fitting function fit to a sliding window applied to a centerline for the vessels in the 3D image volume.

14. The system of claim 1 wherein the velocity of blood flow is a local velocity for each of a plurality of vessels or vessel segments within the 3D image volume.

15. The system of claim 1 wherein the report includes at least one of an image of the 3D image volume with color overlays, graphical overlays, or numerical overlays indicating the quantified flow.

16. A method for creating an image including quantified flow within vessels of a subject, the method including steps comprising:
providing a single-sweep, three-dimensional (3D) image volume acquired from a subject during a single pass of a computed tomography (CT) imaging system as the subject receives a dose of a contrast agent;
determining a phase shift corresponding to pulsatile contrast in vessels within the single-sweep, 3D image volume;
quantifying a flow through the vessels within the single-sweep, 3D image volume using the phase shift; and
generating a report including indicating flow through the vessels within the 3D image volume.

17. The method of claim 16 further comprising generating synthesized non-contrast images from the single-sweep, 3D image dataset.

18. The method of claim 17 further comprising generating an attenuation value representing non-contrast enhanced blood from the single-sweep, 3D image dataset to generate the synthesized non-contrast images from the single-sweep, 3D image dataset.

19. The method of claim 17 further comprising subtracting the 3D image volume and the synthesized non-contrast images from the single-sweep, 3D image dataset.

20. The method of claim 16 further comprising generating time-attenuation curves (TACs) to determine the phase sift corresponding to pulsatile contrast in the vessels.

21. The method of claim 16 further comprising determining a centerline for the vessels within the 3D image volume.

22. The method of claim 21 further comprising determining a cross-profile for points along the centerline.

23. The method of claim 16 further comprising performing a frequency-based analysis to extract only a frequency corresponding to the pulsatile contrast in the vessels.

24. The method of claim 23 further comprising generating time-attenuation curves (TACs) for the vessels in the 3D image volume.

25. The method of claim 24 further comprising applying a one-dimensional Fourier transform to each TAC and calculating an average power spectrum for the vessels in the 3D image volume to determine the phase shift corresponding to pulsatile contrast in vessels within the 3D image volume based on spectral power density.

26. The method of claim 16 further comprising determining the phase shift corresponding to pulsatile contrast in vessels within the 3D image volume based on spectral power density by identifying a peak spectral power density.

27. The method of claim 26 further comprising extracting an angular component at a selected frequency using the peak spectral power density to determine the phase shift corresponding to pulsatile contrast in vessels within the 3D image volume.

28. The method of claim 16 further comprising calculating a velocity of blood flow through vessels within the 3D image volume using a linear fitting function fit to a sliding window applied to a centerline for the vessels in the 3D image volume.

29. The method of claim 16 wherein the velocity of blood flow is a local velocity for each of a plurality of vessels or vessel segments within the 3D image volume.

30. The method of claim 16 wherein the report includes at least one of an image of the 3D image volume with color overlays, graphical overlays, or numerical overlays indicating the quantified flow.

\* \* \* \* \*